(12) United States Patent
Abele et al.

(10) Patent No.: US 8,816,118 B2
(45) Date of Patent: Aug. 26, 2014

(54) DIASTEREOSELECTIVE PREPARATION OF BICYCLO[2.2.2]OCTAN-2-ONE COMPOUNDS

(75) Inventors: Stefan Abele, Allschwil (CH); Jacques-Alexis Funel, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/880,486

(22) PCT Filed: Oct. 19, 2011

(86) PCT No.: PCT/IB2011/054666
§ 371 (c)(1),
(2), (4) Date: Apr. 19, 2013

(87) PCT Pub. No.: WO2012/052943
PCT Pub. Date: Apr. 26, 2012

(65) Prior Publication Data
US 2013/0289295 A1 Oct. 31, 2013

(30) Foreign Application Priority Data

Oct. 20, 2010 (WO) .................. PCT/IB2010/054743

(51) Int. Cl.
*C07C 303/26* (2006.01)
(52) U.S. Cl.
USPC .......................................... 558/44; 548/304.4
(58) Field of Classification Search
USPC ................................ 558/44; 548/301.7, 304.4
See application file for complete search history.

(56) References Cited

U.S. PATENT DOCUMENTS

| 8,202,885 B2 | 6/2012 | Hilpert et al. |
| 8,492,555 B2 * | 7/2013 | Abele et al. ............... 548/309.7 |
| 2011/0039905 A1 | 2/2011 | Hubler et al. |
| 2013/0211104 A1 | 8/2013 | Abele et al. |

OTHER PUBLICATIONS

Bella, M. et al., "Synergic Asymmetric Organocatalysis (SAOc) of Cinchona Alkaloids and Secondary Amines in the Synthesis of Bicyclo[2.2.2]Octan-2-Ones", Chem. Commun., No. 5, pp. 597-599, (2009).
Carreira, E. et al., "Chiral Olefins as Steering Ligands in Asymmetric Catalysis", Angew. Chem. Int., Ed. (2008), vol. 47, pp. 4482-4502.
Funel, J.-A., et al., "Design and Scale-Up of Diels-Alder Reactions for the Practical Synthesis of 5-Phenylbicyclo[2.2.2]Oct-5-En-2-One", Org. Process Res. Dev. (2011), vol. 15, pp. 1420-1427.
Hayashi, T., et al., "$C_2$-Symmetric Bicyclo[2.2.2]Octadienes as Chiral Ligands: Their High Performance in Rodium-Catalyzed Asymmetric Arylation of N-Tosyarylimines", J. Am. Chem. Soc., vol. 126, pp. 13584-13585, (2004).
Hayashi, T., et al., "Chiral Diene Ligands for Asymmetric Catalysis", Aldrichimica Acta., vol. 42, No. 2, pp. 31-38, (2009).
Hill, R. K., et al., "Synthesis and Chiroptical Properties of 5,7-Dioxobicyclo[2.2.2]Oct-2-Ene and Bicyclo[2.2.2]Octane-2,5-Dione", J. Org. Chem., vol. 50, pp. 5528-5533, (1985).
Kinoshita, T., et al., "Synthesis and Racemization via Intermolecular Prototropy of Optically Active Alkyltropylium Ions. A Novel Scale for the Kinetic Brönsted Basicity of Organic Solvents", Tetrahedron Letters, vol. 31, No. 28, pp. 4057-4060, (1990).
Luo, Y., et al., "A Practical Chemo-enzymatic Synthesis of Homochiral Bicyclo[2.2.2]Octane-2,5-Dione", J. Org. Chem., vol. 75, pp. 2057-2060, (2010).
Perry, R. H., et al., "Perry's Chemical Engineers' Handbook", 7th Edition, Table of Contents, McGraw-Hill, (Copyright 1997), ISBN 0-07-049841-5.
Renzi, P., et al., "Multicomponent Asymmetric Reactions Mediated by Proline Lithium Salt", Org. Biomol. Chem., vol. 8, pp. 980-983, (2010).
Werstiuk, N.H., et al., "Synthesis of Bicyclic Diones and Thiones, Facile Methylation of the Enolates of Bicyclo[2.2.1]Heptane-2,5-Dione. An AM1 Computational Study of Bicyclic Enolates", Can. J. Chem., vol. 70, pp. 974-980, (1992).

* cited by examiner

*Primary Examiner* — Golam M M Shameem
(74) *Attorney, Agent, or Firm* — Hoxie & Associates LLC

(57) ABSTRACT

The present invention relates to a new process for the diastereoselective preparation of (1R*,4R*,5S*,6S*)-6-hydroxy-5-arylbicyclo[2.2.2]octan-2-one compounds, the compounds of the formula (II), which may subsequently be further transformed to 5-aryl-bicyclo[2.2.2]oct-5-en-2-one compounds of the formula (I):

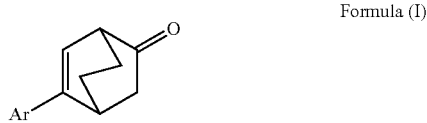

Formula (I)

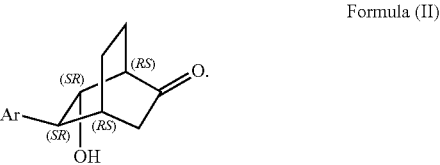

Formula (II)

The present invention further relates to novel (1R*,2S*,3S*,4R*)-6-oxo-3-arylbicyclo[2.2.2]octan-2-yl methanesulfonate compounds as such, which compounds are useful intermediates in the preparation of 5-aryl-bicyclo[2.2.2]oct-5-en-2-one compounds of the formula (I).

20 Claims, No Drawings

DIASTEREOSELECTIVE PREPARATION OF BICYCLO[2.2.2]OCTAN-2-ONE COMPOUNDS

CROSS REFERENCE TO RELATED APPLICATIONS

This application is a United States National Stage Application under 35 U.S.C. 371 of PCT Application No. PCT/IB2011/054666, filed on Oct. 19, 2011, which claims the benefit of PCT Application No. PCT/IB2010/054743, filed Oct. 20, 2010.

FIELD OF THE INVENTION

The present invention relates to a new process for the diastereoselective preparation of (1R*,4R*,5S*,6S*)-6-hydroxy-5-arylbicyclo[2.2.2]octan-2-one compounds, the compounds of the formula (II), which may subsequently be further transformed to compounds of the formula (I):

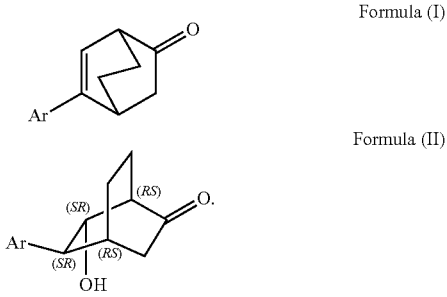

The present invention further relates to novel (1R*,2S*, 3S*,4R*)-6-oxo-3-arylbicyclo[2.2.2]octan-2-yl methanesulfonate compounds of formula (V) as such. The present compounds of formula (V) can be used as intermediates in the preparation of 5-aryl-bicyclo[2.2.2]oct-5-en-2-one compounds of the formula (I). Said compounds of the formula (I) are key building blocks in the synthesis of certain calcium channel blockers described in WO2008/132679 and WO2009/130679. Especially, they can be further transformed to the compound isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester, or the corresponding (1S,2S,4S)-stereoisomer thereof.

Furthermore, compounds of formula (I) can be used for the synthesis of chiral bicyclic dienes of formula (III)

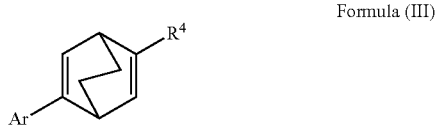

wherein R⁴ represents any group which may be introduced by an organometallic reagent; especially alkyl or aryl. Compounds of formula (III), especially C₂-symmetrical 2,5-disubstituted bicyclo[2.2.2]octa-2,5-dienes (bod*), are rapidly gaining considerable interest as chiral ligands in asymmetric catalysis, see for example: E. Carreira et al., *Angew. Chem. Int. Ed.* 2008, 47, 2-23; T. Hayashi et al., *Aldrichim. Acta.* 2009, 42, 31. The current syntheses generally suffer from very low yields.

Compounds of formula (I) are known from literature (T. Kinoshita, K. Haga, K. Ikai, K. Takeuchi, *Tetrahedron Letters* 1990, 31, 4057-4060), however they are commonly synthesized in multi-step reactions using in the key step a Diels Alder reaction of either 2-(trimethylsiloxy)-1,3-cyclohexadiene with alpha-chloroacrylonitrile (Funel, J.-A.; Schmidt, G.; Abele, S. *Org. Process Res. Dev.* Publication Date (Web): Jun. 27, 2011; Y. Luo, A. J. Carnell, *J. Org. Chem.* 2010, 75, 2057-2060) or with alpha-acetoxyacrylonitrile (N. H. Werstuik, S. Yeroushalmi, H. Guan-Lin, *Can. J. Chem.* 1992, 70, 974-980 and WO2008/132679; WO2009/130679); or a Diels-Alder reaction of hydrochinone and maleic anhydride (R. K. Hill, G. H. Morton, J. R. Peterson, J. A. Walsh, L. A. Paquette, *J. Org. Chem.* 1985, 50, 5528-5533). These methods generally have the racemic bicyclo[2.2.2]octane-2,5-dione as intermediate and generally suffer from very low yield, use expensive and toxic starting materials and/or are not robust for scale up.

A process for the preparation of the compounds of formula (II) is known in literature (M. Bella et al.; "Synergic asymmetric organocatalysis (SAOc) of Chinchona alkaloids and secondary amines in the synthesis of bicyclo[2,2,2]octan-2-ones"; *Chem. Commun.* 2009, 597-599). The described process relates to a sequential one pot (Tandem) Michael addition-aldol cyclization of 2-cyclohexen-1-one and either phenylacetaldehyde or a derivative substituted at the phenyl ring thereof, or 2-phenyl-propionaldehyde (hydratropaldehyde), catalyzed by salts of 5-membered ring amino acids (such as proline, or the cyclic cysteine derived catalyst of structure (IV)). However, the process leads only to high diastereoselectivities (dr<1:10) in combination with moderate enantioselectivities (ee up to 87%) when cinchona alkaloid derivatives such as quinine are used as large chiral bases in combination with the cysteine derived catalyst of structure (IV), wherein chiral base and catalyst are used in amounts of 25 mol % each.

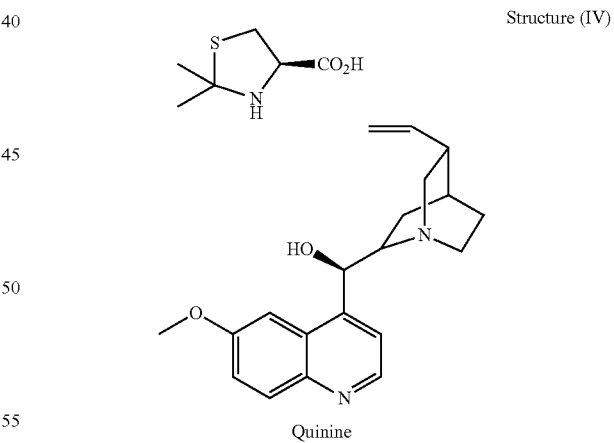

When a small base, e.g. the lithium salt of proline in the absence of a quinine base, is used, the process leads, with the substrate 2-phenyl-propionaldehyde, to low diastereomeric ratios (d.r. 1:1.3) and low enantioselectivities (up to 33% ee). The use of small amine bases [triethylamine or 1,8-diazabicyclo[5.4.0]undec-7-ene (DBU)] as additives, replacing the lithium, lead, again using the same substrate: 2-phenyl-propionaldehyde, to similarly low selectivities. With the substrate phenylacetaldehyde, the use of proline lithium salt gave similar results [low diastereomeric ratio (d.r.=1:4) and low enantioselectivity (up to 17% ee)]. In consequence, small amine bases have not been used with the substrate phenylacetaldehyde. In fact, Bella et al. state that, when proline is used, "achieving high ees on the major diastereoisomer proved challenging [with phenylacetaldehyde as substrate]". The achieved good diastereoselectivities and enantioselectivities using the combination of quinine as large amine base and the amine of structure (IV) are stated to be due to a synergic beneficial effect of the two components of the catalyst system. On page 598 of the above-cited article [in the context of the catalyst of structure (IV)], Bella et al. state that "quinine as co-catalyst not only increased the enantioselectivity to 82% ee, but also induced the preferential formation of one diastereoisomer" and that "magnification of ees is rationalized assuming that a larger cation (protonated quinine instead of Li$^+$) [ . . . ] enhances Re face shielding".

Despite this teaching of Bella et al., it has now surprisingly been found that a highly diastereoselective Tandem Michael addition-aldol cyclization of 2-cyclohexen-1-one and (substituted) phenylacetaldehyde may be catalyzed by proline without the use of the cost intensive chiral quinine bases. The process may be conducted by using a commercially more readily available catalyst system consisting of proline and an achiral base, especially in presence of a small and non-expensive achiral N-containing (nitrogen containing) base, or even by using proline in absence of any base at all.

The present process leads to the precipitation of the desired diastereoisomer, which is then isolated by solid-liquid separation, providing the desired diastereoisomer of the compounds of formula (II) in a scalable way in good yields and high diastereoselectivity. The process may lead to enantiomerically enriched products in case enantiomerically enriched proline is used. The stereoselection is steered only by the absolute configuration of the proline, i.e. the use of D-proline produces compounds of formula (II) with opposite absolute configuration as compared to the use of L-proline. No synergistic contribution of a chiral base is necessary. Simple recrystallization of the enantiomerically enriched product may significantly further increase the enantiomeric excess.

The process of the present invention is scalable and can be performed under surprisingly simple conditions giving rise to a significant reduction of unit operations. In addition, the process may be extended by a two-step reaction, which comprises, as a key step, a surprisingly mild and scalable elimination reaction, to obtain useful building blocks of formula (I) in enantiomerically enriched form. Such process is not disclosed in the above-cited literature.

DESCRIPTION OF THE INVENTION

1) In a first embodiment, the invention relates to a diastereoselective process for the synthesis of (1R*,4R*,5S*,6S*)-6-hydroxy-5-arylbicyclo[2.2.2]octan-2-one compounds, the compounds of the formula (II) (whether in racemic form or in enantiomerically enriched form):

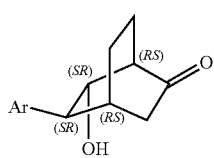

Formula (II)

said process comprising a cyclization of:
2-cyclohexen-1-one, and
a compound of the formula Ar—CH$_2$—CHO, wherein Ar represents an aryl group; in the presence of
 proline (whether in racemic form or in enantiomerically enriched form); and
 a solvent selected from the group consisting of an aromatic solvent, an ether solvent, a chlorinated organic solvent, and an ester; or a mixture thereof; wherein said solvent is present in an amount of about 1 to 10 vol (notably about 3 to 10 vol) with respect to 2-cyclohexen-1-one;
and optionally in the presence of an achiral base;
wherein said compound of formula (II) is isolated from the reaction mixture by solid-liquid separation.

The process of embodiment 1) is a diastereoselective process. It usually leads to isolated (1R*,4R*,5S*,6S*)-6-hydroxy-5-arylbicyclo[2.2.2]octan-2-one compounds in diastereomeric ratio [with respect to the sum of further diastereoisomers: (1R*,4R*,5R*,6R*)-6-hydroxy-5-arylbicyclo[2.2.2]octan-2-one, (1R*,4R*,5R*,6S*)-6-hydroxy-5-arylbicyclo[2.2.2]octan-2-one, (1R*,4R*,5S*,6R*)-6-hydroxy-5-arylbicyclo[2.2.2]octan-2-one] of greater than 90:10, notably greater than 95:5, especially greater than 99:1. In a particular embodiment, diastereoisomerically essentially pure compounds of formula (II) are isolated.

The process of embodiment 1) is optionally performed in the presence of an achiral base. Preferably the process is conducted in absence a chiral base (which is more costly and not required to achieve the high diastereoselectivity of the present process). Especially, the process is conducted either in the presence of an achiral base, or in absence of a base at all. Even though not preferred, the use of chiral bases, e.g. in a mixture with an achiral base, is within the scope of the process of present invention, as its diastereoselectivity would not be negatively effected by the presence of such chiral base. Suitable as achiral base is any achiral base, especially preferred are well known bases which are commercially available implicating low cost of goods. Preferably, such base, when added to the reaction mixture, leads to a pH of about 7 to 10 (especially 8 to 10) in the reaction mixture. Preferred examples of such bases are achiral N-containing bases, aqueous base solutions, or aqueous buffer solutions; or mixtures thereof. An achiral N-containing base notably is selected from the group consisting of tertiary amine bases like NR$^1$R$^2$R$^3$, wherein R$^1$, R$^2$, and R$^3$ independently represent alkyl; 1,4-diazabicyclo[2.2.2]octane (DABCO); amidine bases like 1,8-diazabicyclo[5.4.0]undec-7-en (DBU) or 1,5-diazabicyclo(4.3.0)non-5-ene (DBN) and pyridine, wherein the pyridine is unsubstituted (preferred), or mono-, di-, or tri-substituted with methyl. Such achiral N-containing base is usually present in an amount of about 0.1 equ. to 0.5 equ. with respect to 2-cyclohexen-1-one. An aqueous base solution may be an aqueous solution of said achiral N-containing base; or it is notably an alkali metal hydroxide solution such as especially aqu. NaOH or aqu. KOH. Such aqueous base is usually present in an amount of about 0.05 equ. to 0.3 equ. with respect to 2-cyclohexen-1-one. An aqueous buffer solution is notably sodium phosphate buffer (for example 20 mM Na$_3$PO$_4$ buffer, pH 8) or other aqueous buffer systems known to the person skilled in the art. Such aqueous buffer is usually present in an amount of about 0.4 to 1 vol. with respect to 2-cyclohexen-1-one. In case mixtures are used, such mixtures are preferably mixtures of an achiral N-containing base and an aqueous buffer solution. In such mixtures, the achiral N-containing base is usually present in an amount of about 0.1 equ. to 0.5 equ.; and the aqueous buffer is usually present in an amount of about 0.4 to 1 vol.; both with respect to 2-cyclohexen-1-one. The process of embodiment 1) may also be performed in absence of a base at all.

Commercially available proline (whether in racemic form or in enantiomerically enriched form) is used, usually in amounts of about 0.1 to 0.5 equ. Although not per se part of the present invention, the following is noted for a better understanding thereof: It has been found that alternatively proline may be replaced by proline esters such as methyl prolinate.

Solvents that are used for the process of embodiment 1) are aromatic solvents such as toluene, and anisol; ether solvents such as tert. butyl methyl ether (TBME), tetrahydrofurane (THF), dioxane, and 2-methyl-THF; chlorinated organic solvents such as dichloromethane, 1,2-dichloroethane, chlorobenzene, and 1,2-dichlorobenzene; or esters such as ethyl acetate, isopropyl acetate, and n-butyl acetate; or mixtures of such solvents. Preferred solvents are aromatic solvents such as notably toluene; and ether solvents such as notably tert. butyl methyl ether (TBME). All solvents can be used as purchased without additional drying procedures.

2) In a second embodiment, the process according to embodiment 1) is performed in the presence of an achiral base selected from the group consisting of:
- an achiral N-containing base;
- an aqueous base or an aqueous buffer solution; and
- a mixture of an achiral N-containing base and an aqueous buffer solution.

3) In a third embodiment, the process according to embodiments 1) or 2) is performed in the presence of
- an aqueous base or an aqueous buffer solution; or
- a mixture of an achiral N-containing base and an aqueous buffer solution.

Such process according to embodiment 3) leads to the compounds of formula (II) in high diastereoisomeric purity, but no enantiomeric enrichment is observed even when enantiomerically enriched proline is used. Such process leading to racemic compounds of formula (II) may be a preferred process in case the compounds of formula (II) need to be obtained in racemic form, but, e.g. for commercial reasons, the use of enantiomerically enriched D-, or L-proline is preferred. Such process is preferably performed in an ether solvent (notably TBME) or an aromatic solvent (notably toluene), or mixtures thereof. The following embodiments 7) to 36) below apply mutatis mutandis to such non-enantioselective process of embodiment 3).

Further embodiments of the invention are presented hereafter:

4) In a fourth embodiment, the process according to embodiment 1) is performed in the presence of an achiral N-containing base or in absence of a base.

Such process according to embodiment 4) is performed in the presence of an achiral N-containing base in the absence of chiral base, added aqueous base or aqueous buffer solutions; or in the absence of any added base, especially in absence of any chiral base, added aqueous base or aqueous buffer solutions; in a solvent or solvent mixture according to embodiment 1), in the absence of added water. Such process according to embodiment 4) leads to the compounds of formula (II) in high diastereoisomeric purity as described above.

In addition, in case enantiomerically enriched proline is used, enantiomerically enriched compounds of formula (II) are obtained.

5) In a further embodiment, the process according to embodiment 1) is performed in the presence of an achiral N-containing base.

Such process according to embodiment 5) is performed in the presence of an achiral N-containing base in the absence of added aqueous base or aqueous buffer solutions, especially in a solvent according to embodiment 1), in the absence of added water. Such process according to embodiment 5) leads to the compounds of formula (II) in high diastereoisomeric purity as described above.

In addition, in case enantiomerically enriched proline is used, enantiomerically enriched compounds of formula (II) are obtained.

6) In a further embodiment, the process according to embodiment 1) is performed in the absence of a base.

Such process according to embodiment 6) is performed in the absence of any added base, especially in absence of any chiral base, but also in absence of an achiral N-containing base and in the absence of added aqueous base or aqueous buffer solutions, especially in a solvent according to embodiment 1), notably in the absence of added water. Such process according to embodiment 6) leads to the compounds of formula (II) in high diastereoisomeric purity as described above.

In addition, in case enantiomerically enriched proline is used, enantiomerically enriched compounds of formula (II) are obtained.

7) Another embodiment relates to the process according to embodiment 4) to 6), wherein said process is performed in the presence of enantiomerically enriched D- or L-proline (especially, essentially pure D-proline, or notably L-proline).

In a sub-embodiment, in case said process is performed in the presence of L-proline, the compound of formula (IIa) is obtained in enantiomerically enriched form, or, in another sub-embodiment, in case said process is performed in the presence of D-proline, the compound of formula (IIb) is obtained in enantiomerically enriched form:

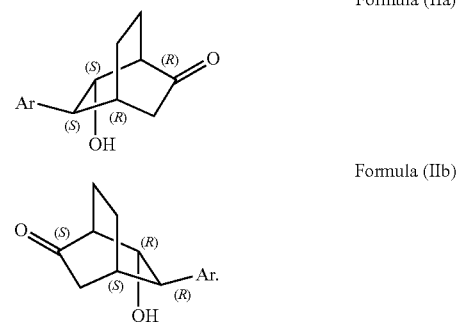

8) Another embodiment relates to the process according to embodiments 4) to 7), wherein the enantiomeric ratio is at least about 60:40 (notably at least about 70:30).

For avoidance of any doubt, in case said process is performed in the presence of L-proline, the enantiomeric ratio refers to the ratio of compound of formula (IIa):compound of formula (IIb); and, in case said process is performed in the presence of D-proline, the enantiomeric ratio refers to the ratio of compound of formula (IIb):compound of formula (IIa); both ratios being at least about 60:40 (notably at least about 70:30).

9) Another embodiment relates to the process according to any one of embodiments 4) to 8), wherein, in case said process is performed in the presence of enantiomerically enriched proline (especially L-proline), the isolated enantiomerically enriched compound of formula (II) is, in a subsequent step, recrystallized. Preferably, the solvent for such recrystallization is selected from the group consisting of an ether (notably THF), acetonitrile, a ketone (notably acetone), and an alcohol (notably ethanol). Notably, the solvent is THF or acetonitrile, especially THF.

10) Another embodiment relates to the process according to embodiment 9), wherein the enantiomeric ratio of the compound of formula (II), obtained from said recrystallization, is at least about 90:10 (notably at least about 95:5).

11) Another embodiment relates to the process according to any one of embodiments 1) to 10), wherein said process is performed in the presence of an aromatic solvent (notably toluene), or an ether solvent (notably TBME).

12) Another embodiment relates to the process according to any one of embodiments 1) to 10), wherein said process is performed in the presence of an aromatic solvent (notably toluene).

13) Another embodiment relates to the process according to any one of embodiments 4) to 12), wherein said solvent essentially does not contain water.

14) Another embodiment relates to the process according to any one of embodiments 1) to 13), wherein the process is performed at a temperature of about 0° C. to 55° C. (especially at about 30° C. to 50° C., notably at about 45° C.).

15) Another embodiment relates to the process according to any one of embodiments 2) to 14), wherein, if present, said achiral N-containing base has a molecular weight of below about 200.

16) Another embodiment relates to the process according to any one of embodiments 2) to 14), wherein, if present, said achiral N-containing base is selected from the group consisting of $NR^1R^2R^3$, wherein $R^1$, $R^2$, and $R^3$ independently represent alkyl; 1,4-diazabicyclo[2.2.2]octane (DABCO); 1,8-diazabicyclo[5.4.0]undec-7-en (DBU), 1,5-diazabicyclo(4.3.0)non-5-ene (DBN); and pyridine, wherein the pyridine is unsubstituted (preferred), or mono-, di-, or tri-substituted with methyl.

17) Another embodiment relates to the process according to any one of embodiments 2) to 14), wherein, if present, said achiral N-containing base is selected from the group consisting of triethylamine, diisopropyl-ethylamine, tributylamine, trioctylamine, 1,4-diazabicyclo[2.2.2]octane (DABCO), 1,8-diazabicyclo[5.4.0]undec-7-en (DBU), and pyridine.

18) Another embodiment relates to the process according to any one of embodiments 1) to 17), wherein, if present, said achiral N-containing base is selected from the group consisting of triethylamine, diisopropyl-ethylamine, and tributylamine (especially triethylamine, and diisopropyl-ethylamine).

19) Another embodiment relates to the process according to any one of embodiments 1) to 18), wherein, if present, said achiral N-containing base is present in an amount of about 0.1 equ. to 0.5 equ. (notably about 0.2 equ. to 0.3 equ.; especially about 0.25 equ.) with respect to 2-cyclohexen-1-one.

20) Another embodiment relates to the process according to any one of embodiments 1) to 19), wherein proline is present in an amount of about 0.05 equ. to 0.5 equ. (notably about 0.2 equ. to 0.3 equ.; especially about 0.25 equ.) with respect to 2-cyclohexen-1-one.

21) Another embodiment relates to the process according to any one of embodiments 1) to 20), wherein said compound of the formula Ar—CH$_2$—CHO is present in an amount of about 1 equ. to 2 equ. (notably about 1 equ. to 1.3 equ.; especially about 1.1 equ.) with respect to 2-cyclohexen-1-one.

22) Another embodiment relates to the process according to any one of embodiments 1) to 21), wherein said solvent is present in an amount of about 3 to 10 vol (especially about 5 to 7 vol) with respect to 2-cyclohexen-1-one.

23) Another embodiment relates to the process according to any one of embodiments 1) to 22), wherein the process is performed for at least 24 h (notably for about 24 h to 10 days; especially for about 4 days).

24) Another embodiment relates to the process according to any one of embodiments 1) to 23), wherein, in case an achiral base is used, the pH of the reaction mixture is about 8 to 10.

In a sub-embodiment; in case the achiral base consists of an aqueous base or an aqueous buffer solution, or of a mixture of an achiral N-containing base and an aqueous buffer solution; the pH of the reaction mixture is especially about 9 to 10.

In another sub-embodiment; in case the achiral base consists an achiral N-containing base; the pH of the reaction mixture is especially about 8 to 9. In case no base is used at all, the pH of the reaction mixture is usually about 6 to 8.

25) Another embodiment relates to the process according to any one of embodiments 1) to 24), wherein said compound of formula (II) is formed in the reaction mixture in a diastereoisomeric ratio of greater than about 70:30 (notably greater than about 80:20, especially greater than 90:10).

For avoidance of any doubt, in embodiment 25), the term diastereoisomeric ratio of the compound of formula (II) as "formed in the reaction mixture" refers to the diastereomeric ratio as observed using in process control measurements of the reaction mixture. The term diastereomeric ratio with reference to a compound of formula (II) refers to the ratio of the compound of formula (II):(1R*,4R*,5S*,6S*)-6-hydroxy-5-arylbicyclo[2.2.2]octan-2-one (whether in racemic form or in enantiomerically enriched form, thus corresponding to the compound of formula (IIa) or formula (IIb), or to any mixture thereof), to the sum of further diastereoisomers: (1R*,4R*,5R*,6R*)-6-hydroxy-5-arylbicyclo[2.2.2]octan-2-one, (1R*,4R*,5R*,6S*)-6-hydroxy-5-arylbicyclo[2.2.2]octan-2-one, (1R*,4R*,5S*,6R*)-6-hydroxy-5-arylbicyclo[2.2.2]octan-2-one); wherein the compound of structure (dia-II): (1R*,4R*,5R*,6R*)-6-hydroxy-5-arylbicyclo[2.2.2]octan-2-one (whether in racemic form or in enantiomerically enriched form), is generally the most important minor diastereoisomer:

Formula (II)

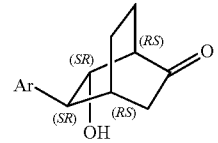

Structure (dia-II)

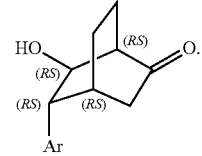

26) Another embodiment relates to the process according to any one of embodiments 1) to 25), wherein said isolation from the reaction mixture by solid-liquid separation is achieved
   by solid-liquid separation (especially filtration) of the precipitated product at the reaction temperature; or
   by
     1. cooling of the reaction mixture to a temperature below the reaction temperature and 2. solid-liquid separation (especially filtration) of the precipitated product.

27) A further aspect of the present invention relates to a process according to any one of embodiments 1) to 26), wherein the compound of the formula (II) is further transformed to a compound the formula (I):

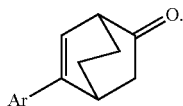

Formula (I)

28) Another embodiment relates to the process according to embodiment 27), wherein said transformation of the compound of the formula (II) to the compound of the formula (I) is effected via an elimination step.

29) Another embodiment relates to the process according to embodiment 28), wherein said elimination step comprises the activation of the alcohol function of the compound of formula (II).

30) Another embodiment relates to the process according to embodiments 28) or 29), wherein the compound of formula (V) [i.e. the compound (1S*,2R*,3R*,4S*)-6-oxo-3-arylbicyclo[2.2.2]octan-2-yl methanesulfonate]:

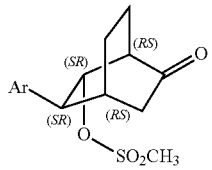

Formula (V)

is an intermediate of said elimination step.

31) Another embodiment relates to the process of any one of embodiments 27) to 30), wherein the compound of formula (I) is obtained in form of the enantiomerically enriched (R,R)-, respectively, (S,S)-isomer of the compound of formula (I):

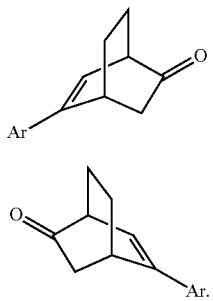

(R,R)-Formula (I)

(S,S)-Formula (I)

For avoidance of any doubt, embodiment 29) especially relates to the process of embodiments 27) to 30) in combination with embodiment 7), wherein the particular conditions of embodiments 8) to 26) apply mutatis mutandis.

32) Another embodiment relates to the process of any one of embodiments 27) to 30), wherein the compound of formula (I) is obtained in racemic form, or as mixture of enantiomers of any ratio; and the enantiomerically enriched (R,R)-, respectively, (S,S)-isomer of the compound of formula (I):

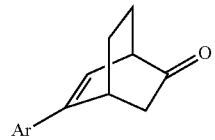

(R,R)-Formula (I)

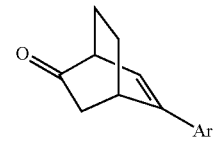

(S,S)-Formula (I)

is obtained by subsequent separation of the enantiomers using preparative chiral HPLC.

For avoidance of any doubt, embodiment 32) especially relates to the process of embodiments 27) to 30) in combination with embodiment 3), or any one of embodiments 4) to 6) wherein proline is used in racemic form.

33) A further aspect of the present invention relates to a process according to any one of embodiments 27) to 32), wherein the compound of the formula (I) is further transformed to a compound the formula (III):

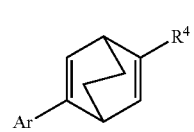

Formula (III)

wherein $R^4$ represents any group which may be introduced by an organometallic reagent (especially organolithium, organomagnesium, or organoboron reagent); especially $R^4$ represents alkyl or aryl.

In a sub-embodiment said transformation is effected either by a sequence of direct addition and elimination; or by the coupling of said organometallic reagent with the respective enol trifluoromethanesulfonate of formula (VI)

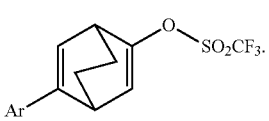

Formula (VI)

34) Another embodiment relates to the process according to embodiment 33), wherein said transformation is effected via an addition-elimination sequence.

35) Another embodiment relates to the process according to embodiment 34), wherein the compound of formula (VII) is an intermediate in said addition-elimination sequence:

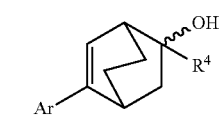

Formula (VII)

wherein said compound of formula (VII) is obtained by an addition reaction of said organometallic reagent to the ketone of the compound of formula (I).

36) Another embodiment relates to the process according to any one of embodiments 33) to 35), wherein $R^4$ is different from Ar; i.e. compound of formula (III) is not $C_2$-symmetrical:

37) Another embodiment relates to the process of any one of embodiments 33) to 36), wherein the compound of formula (III) is obtained in form of the enantiomerically enriched (R,R)-, respectively, (S,S)-isomer of the compound of formula (III):

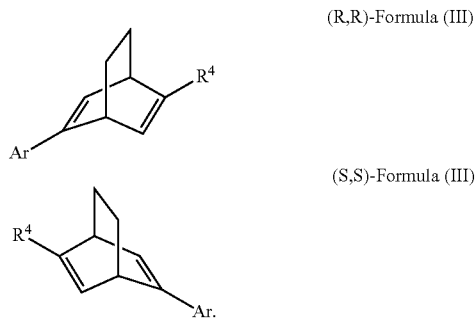

For avoidance of any doubt, embodiment 37) especially relates to the process of embodiment 31).

38) A further aspect of the present invention relates to novel compounds of the formula (V) having the relative configuration (1R*,2S*,3S*,4R*) [i.e. the compound is (1R*,2S*,3S*,4R*)-6-oxo-3-arylbicyclo[2.2.2]octan-2-ylmethanesulfonate]:

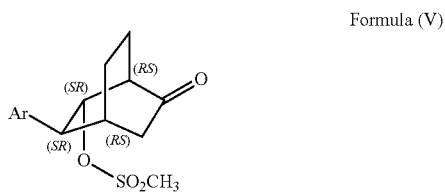

wherein
Ar represents an aryl group.

In a sub-embodiment, said compound of the formula (V) notably is enantiomerically enriched (preferably enantiomerically essentially pure); i.e. the compound is either the enantiomerically enriched compound having absolute configuration (1R,2S,3S,4R), or the enantiomerically enriched compound having absolute configuration (1S,2R,3R,4S).

These compounds are intermediates in the process of embodiment 30).

39) Another embodiment relates to the compounds of formula (V) according to embodiment 38), selected from the group consisting of:
(1R,2S,3S,4R)-6-oxo-3-phenylbicyclo[2.2.2]octan-2-yl methanesulfonate; and
rac-(1R*,2S*,3S*,4R*)-6-oxo-3-phenylbicyclo[2.2.2]octan-2-ylmethanesulfonate.

40) A further aspect of the present invention relates to a process according to any one of embodiments 27) to 32), wherein the compound of the formula (I), wherein in this particular case Ar represents phenyl, is further transformed to any one of the following compounds:
rac-isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester, isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester; or especially
isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester.

Such multistep transformation according to embodiment 40) is described especially in WO2009/130679 (examples 1A, 2A, 3A), which reference is incorporated in its entirety:

In a first step, the compound of formula (I), wherein in this particular case Ar represents phenyl (and wherein it is well understood that said compound of formula (I) may be used in racemic or the appropriate enantiomerically enriched form), is transformed to (1R*,2R*,4R*)-2-hydroxy-5-phenyl-bicyclo[2.2.2]oct-5-en-2-yl)-acetic acid tert.-butyl ester; which in turn is deprotected to the compound (1R*,2R*,4R*)-(2-hydroxy-5-phenyl-bicyclo[2.2.2]oct-5-en-2-yl)-acetic acid; which in turn is coupled with 3-(4,7-dimethoxy-1H-benzoimidazol-2-yl)-propyl]-methyl-amine to give (1R*,2R*,4R*)—N-[3-(4,7-dimethoxy-1H-benzoimidazol-2-yl)-propyl]-2-(2-hydroxy-5-phenyl-bicyclo[2.2.2]oct-5-en-2-yl)-N-methyl-acetamide; which in turn may be reduced to (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-ol; which in turn may be acylated to the compound (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester, which is a calcium channel blocker.

The term "aryl" as used herein means a phenyl or naphthyl group (preferably a phenyl group) which group is unsubstituted (preferred), or mono-, di-, or tri-substituted, wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy.

The term "heteroaryl" means a 5- to 10-membered monocyclic or fused bicyclic aromatic ring containing 1 to a maximum of 4 heteroatoms independently selected from oxygen, nitrogen and sulfur. Examples of monocyclic heteroaryl groups are 5-membered monocyclic heteroaryl groups such as furanyl, oxazolyl, isoxazolyl, oxadiazolyl, thienyl, thiazolyl, isothiazolyl, thiadiazolyl, pyrrolyl, imidazolyl, pyrazolyl, triazolyl, and tetrazolyl; and 6-membered monocyclic heteroaryl such as pyridyl, pyrimidyl, pyridazinyl, and pyrazinyl. Examples of bicyclic heteroaryl groups comprise 8-membered bicyclic heteroaryl groups such as 4H-furo[3,2-b]pyrrolyl, pyrrolo[2,1-b]thiazolyl and imidazo[2,1-b]thiazolyl; 9-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, pyrazolo[1,5-a]pyridyl, pyrazolo[1,5-a]pyrimidyl, imidazo[1,2-a]pyridyl, 1H-pyrrolo[3,2-b]pyridyl, and 1H-pyrrolo[2,3-b]pyridyl; and 10-membered bicyclic heteroaryl groups such as quinolinyl, isoquinolinyl, naphthyridinyl, cinnolinyl, quinazolinyl, quinoxalinyl, and phthalazinyl.

The term "alkyl", used alone or in combination, refers to a saturated straight or branched chain alkyl group containing one to eight carbon atoms. The term "$(C_{x-y})$alkyl" (x and y each being an integer), refers to an alkyl group as defined before containing x to y carbon atoms. For example a $(C_{1-4})$alkyl group contains from one to four carbon atoms. Examples of alkyl groups are methyl, ethyl, propyl, isopropyl, n-butyl, isobutyl, sec.-butyl, and tert. butyl. Preferred are methyl and ethyl. Most preferred is methyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, isopropoxy, n-butoxy, isobutoxy, sec.-butoxy and tert.-butoxy. Preferred are ethoxy and especially methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl and 2,2,2-trifluoroethyl. Preferred are $(C_1)$fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy.

The term "halogen" as used herein means fluoro, chloro, bromo or iodo, preferably chloro.

The term "any group which may be introduced by an organometallic reagent" as used for the substituent $R^4$ means all kinds of residues which may be installed via a organometallic reagent which is capable of making an addition reaction on a ketone carbonyl group. Especially, the term represents any residue which may be introduced using an organolithium, organomagnesium, organoboron, organoaluminium or organozinc reagent; notably organolithium, organomagnesium, or organoboron reagent. Examples of such residues are alkyl; aryl; alkenyl; and alkyl which is substituted with one or more substituents selected from fluoro, alkoxy, aryl, and —CO—$R^5$ wherein $R^5$ is alkyl or alkoxy. In addition, in some instances also heteroaryl groups such as especially 5- or 6-membered heteroaryl may be introduced via an organometallic reagent. Preferred examples of such residues are alkyl and aryl.

The term "alkenyl" as used herein, alone or in combination, refers to a straight or branched hydrocarbon chain containing two to six carbon atoms with at least one carbon-carbon double bond. The term "$(C_{x-y})$alkenyl" (x and y each being an integer), refers to an alkenyl group as defined before containing x to y carbon atoms. Representative examples of alkenyl include, but are not limited to, ethenyl (also referred to as "vinyl"), 2-propenyl (also referred to as "allyl"), 2-methyl-2-propenyl, 3-butenyl, 4-pentenyl, and 5-hexenyl, especially ethenyl or 2-propenyl.

The term "solid-liquid separation" refers to routine solid-liquid separation techniques well known to a skilled person (see for example Perry's Chemical Engineers' Handbook, 7th edition, Perry, R. H.; Green, D. W. McGraw-Hill 1997). In particular, the term includes techniques such as filtration, centrifugation, and gravity sedimentation; especially filtration.

The term "liquid-liquid extraction" refers to routine liquid-liquid extraction or washing techniques well known to a skilled person (see for example Perry's Chemical Engineers' Handbook, 7$^{th}$ edition, Perry, R. H.; Green, D. W. McGraw-Hill 1997). In particular the term includes washing or extraction techniques using settlers, cyclones, centrifuges, mixer-settler, all kinds of continuous contact equipment; distillation: batch and continuous distillation; and supercritical fluid separation techniques.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In case the term about is placed before a range, the respective interval is to be applied to both values of the range. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

The expression % w/w refers to a percentage by weight compared to the total weight of the composition considered. Likewise, the expression v/v refers to a ratio by volume the two components considered. Likewise, the expression % a/a refers to the purity with respect to area under the curve (i.e. integral) in a chromatogram, preferably measuring the UV absorption. The expression "vol" signifies volumes (in L, e.g. of solvent) per weight (in kg, e.g. of reactant). For example 7 vol signifies 7 liters (of solvent) per kg (of reactant).

The term "enriched", for example when used in the context of enantiomers or diastereoisomers is understood in the context of the present invention to mean especially that the respective enantiomer/diastereoisomer is present in a ratio (mutatis mutandis:purity) as explicitly specified; usually in a ratio of at least 60:40, especially of at least 70:30, and notably of at least 90:10 (mutatis mutandis:purity of 60%/70%/90%) with respect to the respective other enantiomer/diastereoisomer. Preferably the term refers to the respective essentially pure enantiomer/diastereoisomer.

The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

The relative configuration of stereoisomers is denoted as follows: for example, (1R*,2S*,3S*,4R*)-6-oxo-3-phenylbicyclo[2.2.2]octan-2-yl methanesulfonate, if not explicitly mentioned as racemate, denominates (1R,2S,3S,4R)-6-oxo-3-phenylbicyclo[2.2.2]octan-2-yl methanesulfonate, or (1S,2R,3R,4S)-6-oxo-3-phenylbicyclo[2.2.2]octan-2-yl methanesulfonate, or any mixture of these two enantiomers.

According to the invention, the compounds of Formulae (I) to (III) may be manufactured by the methods given below. In general, they are prepared according to the general sequence of reactions outlined below in the General Reaction Schemes 1 to 5. Ar has the meaning given in embodiment 1).

General Reaction Scheme 1:

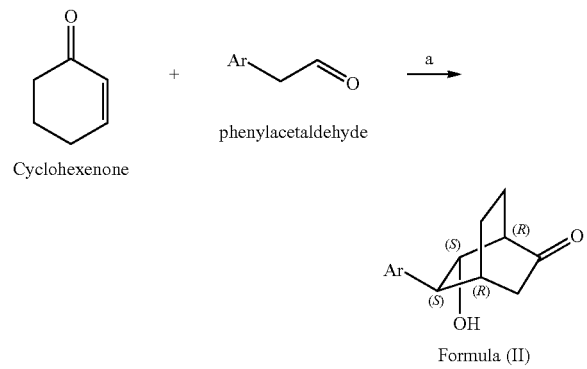

In a first variant of step a, 2-cyclohexen-1-one is reacted with a phenylacetaldehyde in the presence of proline and optionally an achiral N-containing base to obtain compounds of formula (II) [here: corresponding to the enantiomerically enriched diastereoisomer of formula (IIa)]. Typical conditions are as follows: Solvents may be aromatic solvents such as toluene, and anisol; ether solvents such as tert. butyl methyl ether (TBME), tetrahydrofurane (THF), dioxane, and 2-methyl-THF; chlorinated organic solvents such as dichloromethane, 1,2-dichloroethane, chlorobenzene, and 1,2-dichlorobenzene; or esters such as ethyl acetate, isopropyl acetate, and n-butyl acetate. Preferred solvents are aromatic solvents such as toluene; and ether solvents such as tert. butyl methyl ether (TBME). The solvents are used in amounts of 3 to 10 vol. with respect to 2-cyclohexen-1-one, usually 5 to 7 vol. Proline is present in an amount of about 0.05 equ. to 0.5 equ. (usually about 0.25 equ.) with respect to 2-cyclohexen-1-one. The phenylacetaldehyde (Ar—CH$_2$—CHO) is present in an amount of about 1 equ. to 2 equ. (usually about 1.1 equ.) with respect to 2-cyclohexen-1-one. If present, preferred achiral N-containing bases are tertiary amine bases like triethylamine, diisopropylethylamine, or tributylamine. Such achiral N-containing base may be present for example in an amount of about 0.1 equ. to 0.5 equ. with respect to 2-cyclohexen-1-one, usually 0.25 equ. The reaction temperature is 0-55° C., usually 45° C. The reaction is performed for at least 24 h, usually about 4 days. After such time, water is added to the mixture. The amount of water is about 1 to 5 vol. with respect to 2-cyclohexen-1-one, usually about 2 vol. The mixture is then worked up by solid-liquid separation. For example, it may be filtered at the reaction temperature or first cooled to 20-25° C. and then filtered. The filter cake is first washed with water, then with the solvent, e.g. toluene. The amounts for the water and toluene washing steps are 1-3 vol. with respect to 2-cyclohexen-1-one, usually about 1 vol. The washing steps are repeated up to 5 times, usually 3 times. The obtained compound of formula (II) is dried at elevated temperature, usually 45° C. under reduced pressure. The diastereomeric ratio of the compound of formula (II), synthesized according to this protocol is generally higher than 99:1 and the enantiomeric ratio (e.r.) is higher than 60:40.

A subsequent recrystallization of the enantiomerically enriched compound of formula (II) as obtained from the above process, notably from THF (about 10 vol.), usually leads to enantiomeric ratios of at least 90:10.

In a second variant, aqueous bases are used with or without said achiral N-containing bases to produce compounds of formula (II) in racemic form. Typical conditions are as follows: An aqueous base is notably an alkali metal hydroxide solution such as especially aqu. NaOH or aqu. KOH. Such aqueous base is usually present in an amount of about 0.05 equ. to 0.3 equ. with respect to 2-cyclohexen-1-one, usually 0.25 equ. An aqueous buffer solution is notably sodium phosphate buffer (for example 20 mM Na$_3$PO$_4$ buffer, pH 8) or other aqueous buffer systems known to the person skilled in the art. Such aqueous buffer is present in an amount of about 0.4 to 1 vol. with respect to 2-cyclohexen-1-one, usually 0.7 vol. In case mixtures are used, such mixtures are preferably mixtures of an achiral N-containing base and an aqueous buffer solution. In such mixtures, the achiral N-containing base is present in an amount of about 0.1 equ. to 0.5 equ., usually 0.25 equ.; and the aqueous buffer is present in an amount of about 0.4 to 1 vol., usually 0.7 vol.; both with respect to 2-cyclohexen-1-one. The reaction is performed for at least 24 h, usually 1-4 days.

The technical advantage of step a is:
The compounds are obtained in high diastereomeric purity.
A commercially readily available and cheap catalyst system is used.
The synthesis is simple, efficient and amenable to large scale.
Enantiomerically enriched or racemic compounds of formula (II) can be obtained by choosing the appropriate reaction conditions.
Enantiomerically enriched compounds of formula (II) can be further enriched by a subsequent recrystallization step.

General Reaction Scheme 2:

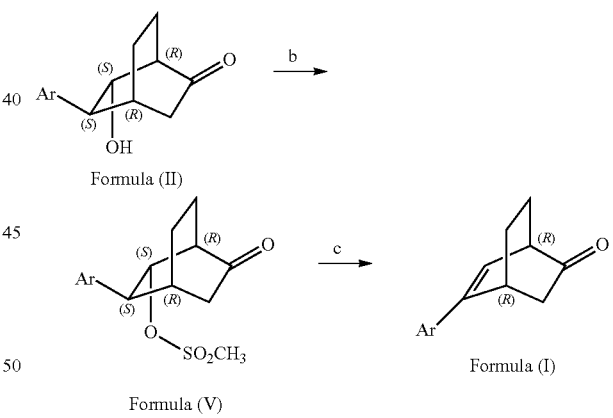

In step b, compounds of formula (II) [here: corresponding to the enantiomerically enriched diastereoisomer of formula (IIa)] are transformed into the corresponding mesylate derivatives of formula (V), in the presence of a base. Typical conditions are as follows: Suitable solvents are aromatic solvents (such as toluene or benzene), ethers (such as THF, 2-methyltetrahydrofurane, 1,4-dioxane or tert-butylmethylether), polar aprotic solvents (such as DMSO, DMF, N-methylpyrrolidinone or dimethylacetamide) or chlorinated hydrocarbons (such as DCM). Most preferred solvent is toluene. The preferred reagent is methanesulfonyl chloride which is used in about 1-2 equ. per equ. of the compound of formula (II), usually in about 1.3 equ. Appropriate bases are triethylamine, diethylisopropylamine or pyridine in amounts of about 1.5-3 equ. per equ. of the compound of formula (II), usually in about 1.5 equ. The reaction is usually carried out at about 10-25° C. for about 10-60 min. After completion of the reaction water is added, followed by phase separation and a solvent exchange to the solvent of step c. Alternatively, the activation can be achieved by reacting the compound of formula (II) with benzoyl chloride in the presence of triethylamine in DCM at r.t. Alternatively, compounds of formula (V) can be obtained in crystalline form by crystallization from heptane/EtOAc (1:1 v/v) or toluene.

In step c, compounds of formula (V) are transformed into compounds of formula (I) [here: corresponding to the enantiomerically enriched compound of formula (I)] by elimination of methanesulfonic acid. Suitable solvents are aromatic solvents (such as toluene, benzene, chlorobenzene, or xylenes), polar aprotic solvents (such as DMSO, sulfolane, DMF, N-methylpyrrolidinone or dimethylacetamide), higher boiling nitriles (such as acetonitrile or butyronitrile), higher boiling ethers (such as bis(2-methoxyethyl)ether), higher boiling nitrogen bases (such as 1,8-diazabicyclo[5.4.0]undec-7-en or 1,5-diazabicyclo(4.3.0)non-5-ene), or pyridines (such as pyridine, 2,6-lutidine or 2,4,6-collidine). The reaction is carried out at about 85-160° C., usually at about 100-150° C. The reaction time is varying from 10 min-16 h, usually it is about 0.5-2 h.

In a preferred variant, the reaction step c is performed in the presence of bases using the solvents mentioned above. In this case, when basic solvents such as the above mentioned higher boiling nitrogen bases or pyridines are used, such solvents may serve at the same time as solvent and as base. Generally, suitable bases are amidine or guanidine bases (such as 1,8-diazabicyclo[5.4.0]undec-7-ene, 1,5-diazabicyclo(4.3.0)non-5-ene, 7-methyl-1,5,7-triazabicyclo[4.4.0]dec-5-ene), tertiary amines (such as 1,4-diazabicyclo[2.2.2]octane or tetramethylpropylene diamine), inorganic bases (such as potassium carbonate, lithium carbonate), or alcoholates (such as lithium-, sodium- or potassium salts of methanol, ethanol or tert-butyl alcohol). The bases are used in amounts of about 1-10 equ. per equ. of the compound of formula (V), usually about 1-2 equ. When used as solvent and base at the same time, such bases are used in amounts of about 1-15 vol, notably 5-10 vol, with respect to the compound of formula (V). Potential additives are iodides (such as NaI) or lithium salts (such as LiBr), used in amounts of about 0.1-1 equ. per equ. of the compound of formula (V). In a particular variant, the elimination is accomplished in the presence of 2 equ. of 1,8-diazabicyclo[5.4.0]undec-7-ene in toluene at about 140° C. for about 1 h. In another particular variant, the elimination is accomplished in the presence of about 1.5 equ. of $Li_2CO_3$ in 1,8-diazabicyclo[5.4.0]undec-7-ene at about 100° C. for about 0.5 h.

In a second variant, the reaction step c is carried out without a base, in the presence of silicium dioxide in DMSO.

In a third variant, the reaction step c is carried out without a base by heating the compound of formula (V) in a suitable solvent like o-xylene, chlorobenzene, 3-dimethyl-3,4,5,6-tetrahydro-2(1H)-pyrimidinone, DMSO, sulfolane, DMF, N-methylpyrrolidinone, pyridine, 2,6-lutidine or 2,4,6-collidine at 140-150° C. for 1-2 h. Preferred solvents for this variant are sulfolane, N-methylpyrrolidinone and especially 2,4,6-collidine. The concentration of the compound of formula (V) is about 0.5-10 vol. (i.e. 0.5-10 L of solvent per equ. of the compound of formula (V)), usually about 1 vol. After completion of the reaction, 1N aqueous HCl is added followed by a suitable solvent (such as iPrOAc, EtOAc, toluene or heptane). Preferred solvents are iPrOAc, EtOAc or heptane. The org. phase is washed with diluted aqu. HCl and dried by azeotropic distillation.

In a preferred variant of step c, the compound of formula (I) is isolated by crystallization from suitable solvents like heptane, tert-butylmethylether, mixtures of heptane and tert-butylmethylether. Preferred solvent for crystallization is heptane.

In a further variant, the steps b and c are telescoped: the compound of formula (V) is thus obtained by simple filtration of the reaction mixture and the filtrate is stirred at about 135° C. for about 1-2 h to obtain compound of formula (I).

Technical advantages of steps b and c:
Step c is highly concentrated, thus enabling a high throughput.
Steps b and c, especially in case the preferred process is used, lead to crude compounds of formula (I) with high chemical purity, thus enabling a further upgrade in purity by crystallization, especially in case the compound of formula (I) is a low melting solid which may be difficult to crystallize in case the crude product has low purity.
The two steps b and c can be telescoped and run in one pot, thus raising the efficiency.

General Reaction Scheme 3:

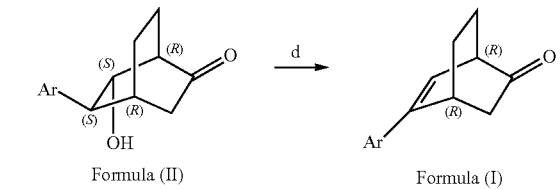

Formula (II)   Formula (I)

Alternatively, compounds of formula (II) can be transformed into compounds of formula (I) without the intermediate formation of the compound of formula (V). In step d, the compounds of formula (II) are treated with suitable Bronsted or Lewis acids (such as acetic acid in combination or not with sodium acetate, polyphosphoric acid, thionyl chloride, phosphorylchloride, or diisopropylcarbodiimide in the presence of copper(I)chloride) in a solvent or neat, at about 50-150° C. for about 1-16 h. A preferred reagent is thionyl chloride. In this case, the reaction is carried out neat at about 50° C. for about 3 h.

General Reaction Scheme 4:

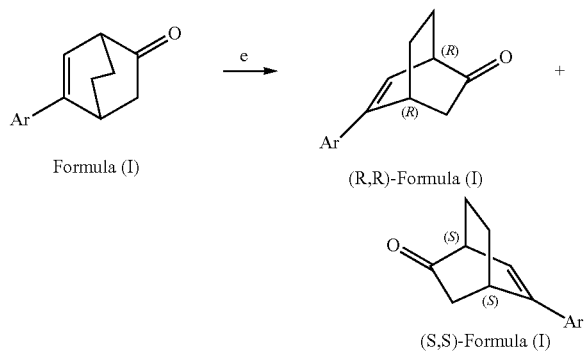

Formula (I)   (R,R)-Formula (I)

(S,S)-Formula (I)

Alternatively, in step e, racemic compounds of formula (I) can be separated in the two respective enantiomers: (R,R)- formula (I) and (S,S)-formula (I), by chromatography on chiral phase. Suitable solvents are mixtures of hydrocarbons and esters such as n-heptane and EtOAc, preferably 75:25 v/v; alternatively with 0.01-0.3% of triethylamine. In addition, methanol can be used as eluent (preferably with 0.01-0.3% of triethylamine). Suitable columns comprise Chiralpak AS-V or Chiralpak IA (e.g. 20 μm).

The technical advantage of step e is:
Both enantiomers are accessible, especially when used for the preparation of compounds of formula (III).
The separation on chiral stationary phase is highly efficient.

General Reaction Scheme 5:

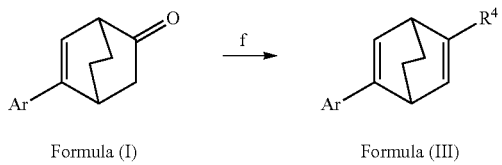

Formula (I)    Formula (III)

In step f, compounds of formula (I) may be transformed into compounds of formula (III). This can either be accomplished similar to published procedures (whereas the diketones are the substrates, using first the synthesis of the enol triflate which is then coupled with Grignard reagents in the presence of e.g. a Pd catalyst, see Hayashi et al., *J. Am. Chem. Soc.* 2004, 126, 13584) or by the successive treatment of (first substep) an organometallic reagent, followed (in a second substep) by dehydration. Suitable organometallic reagents are organolithium, organomagnesium, or organoboron compounds, preferably organomagnesium reagents (Grignard reagents). Additional metal salts can be added like cerium trichloride or lanthanum trichloride, zinc dichloride, copper chloride, lithium chloride, (trimethylsilyl)magnesium chloride, magnesium chloride. The reaction with the organometallic reagent is performed between −80° C. and 30° C., preferably between −10 and 30° C. Suitable solvents for the first substep are ethers (like THF or 2-methyl THF, dimethoxymethane) and aromatic solvents (like toluene), preferably THF or toluene and mixtures thereof. In the second substep the intermediate is either treated with an acid, preferably aqu. mineral acids, most preferably aqu. HCl; or with a sulfonylchloride, especially methanesulfonylchloride. The second substep is carried out at 20-100° C., usually at 20-40° C. Aqu. work-up affords the dienes which can be further purified by either chromatography or crystallization. In a variant, the compound of formula (I) may be added to the organometallic reagent. The processes depicted in general reaction scheme 5 may similarly be used for enantiomerically enriched compounds to afford enantioenriched compounds of formula (III).

The technical advantages of step f is:
Flexibility exists in the synthesis of either $C_r$ or $C_2$-symmetrical chiral dienes with so far unprecedented effects on catalysis.
The following examples further illustrate the invention.

EXAMPLES

All temperatures given are external temperatures and are stated in ° C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); internal standard for quantitative NMR was 1,4-dimethoxybenzene; by LC-MS, and chiral HPLC (methods defined below); $t_R$ is given in minutes. Melting point is measured on Büchi melting point apparatus B540 and is not corrected. Unless stated otherwise, yields are given as is. Corrected yields are corrected with the NMR assay with internal standard of the starting material and the product.

LC-MS Method 1:

| Agilent G1956B (MS, Ionisation: ESI+, APCI), Agilent G1312B Bin Pump, Agilent G1315C DAD, Agilent G1316B (thermostated column compartment), Agilent G1367C (auto sampler) | |
|---|---|
| Injection volume: | 2 μL |
| Column: | Kinetex C18, 2.6 μm, 2.1 × 50 mm |
| Column flow: | 1 ml/min |
| Eluent: | Eluent A: Water, 0.08% TFA (trifluoroacetic acid) |
| | Eluent B: Acetonitrile, 0.012% TFA |
| Gradient: | 2.0 min   95% B |
| | 2.8 min   95% B |
| | 3.0 min   5% B |
| Pressure: | 380 bar |
| Temperature: | 40° C. |
| Detection wavelength: | 210 nm |

LC-MS Method 2:

| Same hardware as LC-method 1 | |
|---|---|
| Injection volume: | 2 μL |
| Column: | Eclipse Plus C18, 1.8 μm, 2.1 × 50 mm |
| Column flow: | 1 ml/min |
| Eluent: | Eluent A: Water, 0.08% TFA (trifluoroacetic acid) |
| | Eluent B: Acetonitrile, 0.012% TFA |
| Gradient: | 2.0 min   95% B |
| | 2.8 min   95% B |
| | 3.0 min   5% B |
| Pressure: | 480 bar |
| Temperature: | 50° C. |
| Detection wavelength: | 210 nm |

Chiral HPLC Method:

| Dionex HPG-3400SD Bin pump, Dionex DAD-3000 | |
|---|---|
| Injection volume: | 2 μL |
| Column: | ChiralPak AS-H, 4.6 × 250 mm, 5 m |
| Column flow: | 0.8 ml/min |
| Eluent: | Heptane (60%)/2-propanol (40%) |
| Concentration: | 4 mg/mL heptane/2-propanol 1:1 |
| Detection: | 210 nm |
| Temperature: | 25° C. |

Abbreviations (as Used Herein and in the Description Above):

| aqu. | aqueous |
| DCM | Dichloromethane |
| DMF | Dimethylformamide |
| DMSO | Dimethylsulfoxide |
| d.r. | Diastereomeric ratio |
| DSC | Differential Scanning Calometry |
| ee | Enantiomeric excess |
| equ. | equivalent(s) |
| e.r. | Enantiomeric ratio |
| EtOAc | Ethyl acetate |
| h | hour(s) |
| iPrOAc | isopropyl acetate |

-continued

| | |
|---|---|
| IPC | In Process Control |
| LC-MS | Liquid Chromatography - Mass Spectrometry |
| GC-MS | Gas Chromatography - Mass Spectroscopy |
| min. | minute(s) |
| m.p. | melting point |
| Ms | Methanesulfonyl (mesyl, $-SO_2-CH_3$) |
| org. | organic |
| rac. | rac. |
| r.t. | room temperature |
| soln. | solution |
| TBME | tert-butyl methyl ether |
| temp. | temperature |
| THF | Tetrahydrofurane |
| TLC | Thin Layer Chromatography |
| $t_R$ | retention time |
| % w/w | Mass % (NMR assay) |
| % a/a | Area % (purity by area %) |

Example 1

Preparation of (1R,4R,5S,6S)-6-hydroxy-5-phenylbicyclo[2.2.2]octan-2-one (Compound 2)

General Method 1:

Scheme 1: Step a (general method)

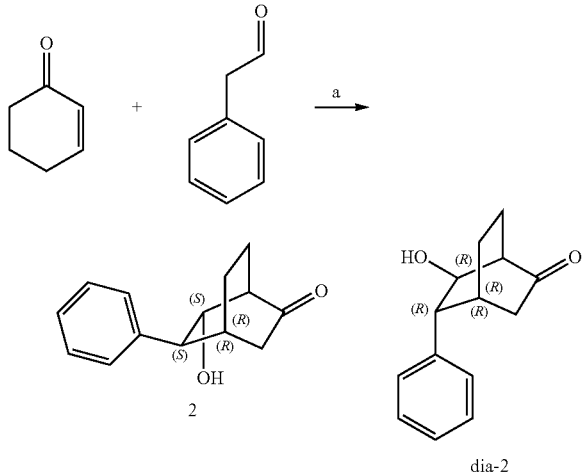

To a mixture of 2-cyclohexen-1-one (1 wt., 1 equ.) and phenyl acetaldehyde (1.1 equ.) in toluene (7 vol.) was added under nitrogen L-proline (0.25 equ.), followed by the base (0.25 equ.) at 20-25° C. The mixture was stirred for 4 d at 45° C. The suspension was cooled 20-25° C., water (2 vol.) was added and the mixture was stirred for 15 min at 20-25° C. The suspension was filtered and washed with water (3×1 vol.), followed by toluene wash (3×1 vol.). The filter cake was dried under vacuum at 45° C. to yield compound 2.

General Method 2:

To a mixture of 2-cyclohexen-1-one (1 wt., 1 equ.) and phenyl acetaldehyde (1.1 equ.) in the specified solvent (6 vol.) was added under nitrogen L-proline (0.25 equ.) at 20-25° C. The mixture was stirred for 3 d at 45° C. The suspension was cooled 20-25° C., water (2 vol.) was added and the mixture was stirred for 15 min at 20-25° C. The suspension was filtered and washed with water (3×1 vol.), followed by a washing step with the specified solvent (3×1 vol.). The filter cake was dried under vacuum at 45° C. to yield compound 2.

Analysis by $^1$H- and $^{13}$C NMR, LC-MS method 1 and chiral HPLC. Diastereomeric ratio (ratio of 2:dia-2; other diastereoisomers<0.5% according to chiral HPLC method) and enantiomeric ratio (ratio of 2:ent-2) were determined by chiral HPLC method.

2: Colorless solid; LC-MS method 1: >99% a/a, $t_R$=1.23, [M-18+1]$^+$=199; $^1$H-NMR (CDCl$_3$): δ=7.34-7.42 (m, 4H), 7.27-7.32 (m, 1H), 4.48 (t, J=3.7 Hz, 1H), 2.93-2.97 (m, 1H), 2.58 (q, J=3.1 Hz, 1H), 2.49-2.56 (m, 1H), 2.35-2.44 (m, 2H), 1.87-1.95 (m, 3H), 1.72-1.83 (m, 1H), 1.42-1.53 (m, 1H); $^{13}$C-NMR (CDCl$_3$): δ=215.40, 142.21, 128.60, 127.56, 126.59, 74.37, 52.83, 51.50, 45.55, 34.42, 20.21, 18.22.

TABLE 1

Examples 1A to 1H using the general method 1 (presence of different bases)

| No. | Scale | Conditions (base) | IPC d.r.[1] | Isolated 2 d.r.[2] | Isolated 2 e.r.[3] | Isolated 2 (yield) |
|---|---|---|---|---|---|---|
| 1A | 25 g | Diisopropyl ethylamine | N.A. | 100:0 | 74:26 | 29.4 g (53%) |
| 1B | 500 g | Diisopropyl ethylamine[4] | N.A. | 100:0 | 72:28 | 717 g (66%) |
| 1C | 5 g | 1,8-Diazabicyclo [5.4.0]undec-7-ene (DBU) | N.A. | 100:0 | 62:38 | 3.7 g (33%) |
| 1D | 5 g | Triethylamine | N.A. | 100:0 | 74:26 | 5.9 g (54%) |
| 1E | 5 g | Tributylamine | 92:8 | 100:0 | 70:30 | 5.8 g (53%) |
| 1F | 5 g | 1,4-Diazabicyclo [2.2.2]octane (DABCO) | 84:16 | 100:0 | 75:25 | 4.5 g (41%) |
| 1G | 5 g | Pyridine | 94:6 | 100:0 | 62:38 | 6.0 g (54%) |
| 1H | 5 g | Trioctylamine | 92:8 | 100:0 | 67:33 | 6.4 g (58%) |

[1] Ratio of 2:dia-2 of reaction mixture after 4 d. IPC: sampled well stirred mixture, evaporated sample to dryness. 2 mg of the residue was dissolved in water/acetonitrile (1 mL) for LC-MS.
[2] Ratio of 2:dia-2 of isolated product.
[3] Ratio of 2:ent-2 of isolated product.
[4] Reaction in toluene (6 vol.).

TABLE 2

Examples 1I to 1K using the general method 2 (absence of base).

| No. | Scale | Solvent | IPC d.r.[1] | Isolated 2 d.r.[2] | Isolated 2 e.r.[3] | Isolated 2 (yield) |
|---|---|---|---|---|---|---|
| 1I | 5 g | Toluene | N.A. | 100:0 | 63:37 | 4.5 g (41%) |
| 1J | 5 g | TBME | 66:34 | 100:0 | 62:38 | 3.2 g (29%) |
| 1K | 5 g | EtOAc | 79:21 | 100:0 | 63:37 | 3.5 g (32%) |

[1] Ratio of 2:dia-2 of reaction mixture after 3 d. IPC: sampled well stirred mixture, evaporated sample to dryness. 2 mg of the residue was dissolved in water/acetonitrile (1 mL) for LC-MS.
[2] Ratio of 2:dia-2 of isolated product.
[3] Ratio of 2:ent-2 of isolated product.

1 L) Preparation of (1S,4S,5R,6R)-6-hydroxy-5-phenylbicyclo[2.2.2]octan-2-one (Compound ent-2)

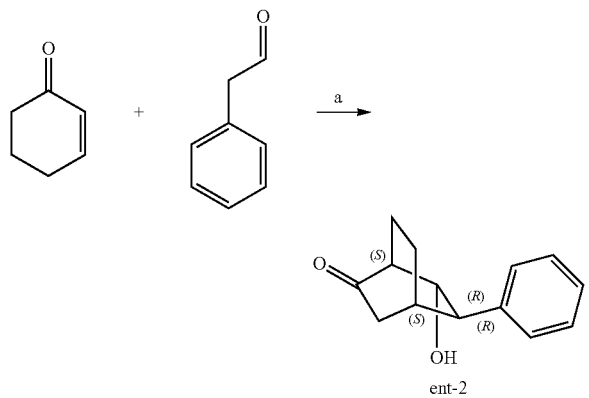

To a mixture of D-proline (2.93 g), N-ethyl-diisopropylamine (4.36 mL) in toluene (70 mL) was added 2-cyclohexen-1-one (10 mL) and phenyl acetaldehyde (14.6 mL) at 20-25° C. The mixture was stirred for 3 d at 45° C. IPC according to LC-MS method 1 indicated>99% conversion. The suspension was cooled to 20-25° C. and filtered. The filter cake was washed with water (3×10 mL), followed by toluene wash (3×10 mL). The filter cake was dried on the filter by sucking air through the filter. Yield: 13.2 g, 60%. $^1$H-NMR (CDCl$_3$) corresponds to structure of compound ent-2. Chiral HPLC method:enantiomeric ratio=27:73 (2:ent-2), diastereomeric purity: 100%; LC-MS method 1: 100% a/a, $t_R$=1.19.

Example 2

Preparation of rac-(1R*,4R*,5S*,6S,*)-6-hydroxy-5-phenylbicyclo[2.2.2]octan-2-one (Compound rac-2)

Example 2A

To a mixture of L-proline (5.87 g), 2-cyclohexen-1-one (20 g) and phenylacetaldehyde (29.9 g, 1.1 equ.) in toluene (140 mL) was added N-diisopropylethylamine (6.6 mL) and 20 mM sodium phosphate buffer soln. (pH 8, 14 mL) at 20-25° C. The mixture was stirred at 45° C. for 10 d. The suspension (pH 8-9) was filtered. The filter cake was washed with water (3×10 mL), followed by toluene wash (3×20 mL). The filter cake was dried at 45° C. under reduced pressure to afford rac-2 as white solid. Yield: 15.7 g, 36%. $^1$H-NMR (CDCl$_3$) corresponds to structure of compound rac-2. Chiral HPLC method:enantiomeric ratio=50:50, diastereomeric purity: 100%; LC-MS method 1: 100% a/a, $t_R$=1.23.

Example 2B

To a mixture of L-proline (1.46 g) in TBME (34 mL) was added 2-cyclohexen-1-one (5 g) and phenylacetaldehyde (8.1 g, 1.2 equ.) at 20-25° C. After addition of 1N NaOH (3.47 mL), the mixture was stirred for 1 d at 20-25° C. The suspension (pH 8-9) was filtered. The filter cake was washed with water (3×5 mL), followed by TBME wash (3×5 mL). The filter cake was dried at 45° C. under reduced pressure to afford rac-2 as white solid. Yield: 2.59 g, 24%. $^1$H-NMR (CDCl$_3$) corresponds to structure of compound rac-2. Chiral HPLC method:enantiomeric ratio=50:50, diastereomeric purity: 100%.

Example 2C

To a mixture of L-proline (1.46 g) in TBME (34 mL) was added 2-cyclohexen-1-one (5 g) and phenylacetaldehyde (13.5 g, 2 equ.) at 20-25° C. After addition of 1N NaOH (3.47 mL), the mixture was stirred for 1 d at 20-25° C. The suspension (pH 8-9) was filtered. The filter cake was washed with water (3×5 mL), followed by TBME wash (2×4 mL). The filter cake was dried at 45° C. under reduced pressure to afford rac-2 as light-yellow solid. Yield: 3.4 g, 32%. $^1$H-NMR (CDCl$_3$) corresponds to the structure of compound rac-2.

Example 3

Recrystallization of Enantiomerically Enriched (1R,4R,5S,6S)-6-hydroxy-5-phenylbicyclo[2.2.2]octan-2-one (Compound 2):

| No. | Scale | Conditions | initial e.r.[1] | isolated e.r.[2] | yield |
|---|---|---|---|---|---|
| 3A | 2 g | THF (10 vol.), reflux, filtration at 20° C. | 74:26 | 94:6 | 26% |
| 3B | 5 g | THF (10 vol.), reflux, filtration at 20° C. | 72:28 | 96:4 | 23% |
| 3C | 5 g | Acetonitrile (32 vol.), reflux, filtration at 20° C. | 72:28 | 100:0 | 9% |
| 3D | 5 g | Acetonitrile (16 vol.), reflux, filtration at 50° C. | 72:28 | 92:8 | 30% |

[1]Ratio of 2:ent-2 of starting material
[2]Ratio of 2:ent-2 of isolated product.

Example 4

Preparation of (1R,4R)-5-phenylbicyclo[2.2.2]oct-5-en-2-one (Compound 1)

Scheme 2: Reaction sequence for the synthesis of compound 1 from compound 2.

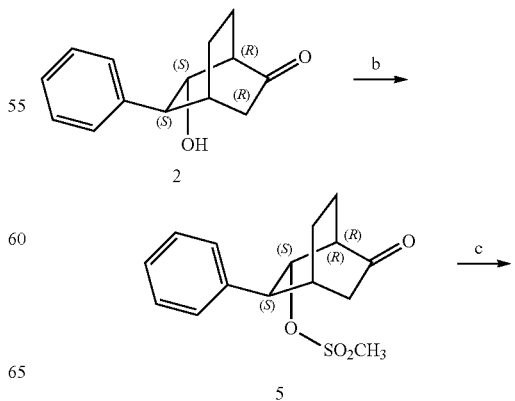

4.1 Preparation of (1R,2S,3S,4R)-6-oxo-3-phenylbicyclo[2.2.2]octan-2-yl methanesulfonate (Compound 5)

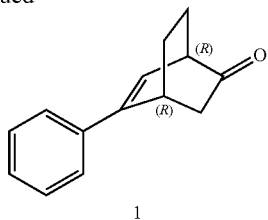

Compound 2 (25 g) was dissolved in DCM (125 mL) followed by triethylamine (24 mL). The suspension was cooled to 0° C. and methane sulfonyl chloride (11.6 mL) was added at 10-20° C. After 1.5 h, the mixture was washed filtered and the filtrate washed with water (3×125 mL). The org. phase was dried over $Na_2SO_4$ and concentrated to dryness under reduced pressure to afford compound 5 as a yellow oil, which solidified at r.t. Yield: 32.5 g, 96%.

20 g thereof were dissolved in heptane (350 mL) and EtOAc (350 ml) at 50° C. and filtered over silica gel (15 g). The filtrate was cooled to 0° C., filtered, and the filter cake was washed with heptane (100 mL) to afford a first crop of compound 5 as a colorless solid. Yield first crop: 8.33 g (42% recovery). Additional crystals were filtered off from the mother liquor to afford a second crop of compound 5 as a colorless solid. Yield second crop: of 2.75 g.

M.p.=87° C. (peak by DSC); LC-MS method 1: 100% a/a, $t_R$=1.4, [M-96+1]+=199; $^1$H-NMR (CDCl$_3$): δ=7.38-7.49 (m, 2H), 7.30-7.38 (m, 3H), 5.45 (t, J=3.8 Hz, 1H), 3.22-3.30 (m, 1H), 2.88-3.00 (m, 4H), 2.54-2.63 (m, 1H), 2.44-2.53 (m, 1H), 2.35-2.42 (m, 1H), 1.96-2.08 (m, 2H), 1.71-1.88 (m, 1H), 1.43-1.60 (m, 1H); $^{13}$C-NMR (CDCl$_3$): δ=210.97, 139.91, 129.03, 127.34, 82.51, 50.59, 48.58, 45.54, 39.45, 35.41, 20.21, 18.02.

4.2 Preparation of (1R,4R)-5-phenylbicyclo[2.2.2]oct-5-en-2-one (Compound 1)

Steps b and c together starting with compound 2 of enantiomeric ratio 72:28.

Compound 2 (100 g, enantiomeric ratio 72:28) was dissolved in toluene (500 mL) followed by triethyl amine (97 mL). The suspension was cooled to 0° C. and methane sulfonyl chloride (46.5 mL) was added at 10-20° C. IPC (LC-MS method 1) showed>99% conversion after 10 min. The mixture was washed with water (2×250 mL) and concentrated to dryness under reduced pressure to afford compound 5 as a light-yellow oil, which solidified at r.t. Yield compound 5: 136 g, 100%. NMR assay: 95% w/w. chiral HPLC method: enantiomeric ratio=72:28; LC-MS method 1: 100% a/a, $t_R$=1.39, [M-96+1]$^+$=199. $^1$H-NMR data in CDCl$_3$ correspond to the structure.

Compound 5 (67.8 g) was dissolved in 2,4,6-collidine (65 mL) and stirred at 140-145° C. for 80 min. 2N HCl (320 mL) and heptane (800 mL) were added and the layers separated. The org. phase was washed with 2N HCl (2×170 mL), then with water (170 mL) and filtered over MgSO$_4$. The filtrate was evaporated to dryness at 50° C. under reduced pressure to afford crude compound 1 as oil.

Yield crude compound 1: 36 g, 79%. Chiral HPLC method: enantiomeric ratio=69:31. LC-MS method 1: 95.2% a/a, $t_R$=1.54; $^1$H-NMR data in CDCl$_3$ correspond to the structure.

This crude product (36 g) was dissolved in TBME (30 mL) at 50° C. After cooling to 0° C., and stirring at 0° C. for 0.5-1 h, the suspension was filtered and the filter cake was washed with TBME (3×3 mL). The product was dried at 50° C. under reduced pressure to afford the first crop cryst1#1 as a colorless solid.

Cryst1#1: 11.95 g, 33% recovery, 26% yield from compound 5. Chiral HPLC method:enantiomeric ratio=98:2. $^1$H-NMR data in CDCl$_3$ correspond to the structure.

The mother liquor of the first crystallization was diluted with heptane (30 ml) and stirred at 0° C. for 0.5 h. The suspension was filtered and the filter cake was washed with TBME (3×1 mL). The product was dried at 50° C. under reduced pressure to afford the second crop cryst1#2 as a colorless solid.

Cryst1#2: 1.63 g, 4%. Chiral HPLC method:enantiomeric ratio=98:2. $^1$H-NMR data in CDCl$_3$ correspond to the structure.

Example 5

Recrystallization of Enantiomerically Enriched (1R,4R)-5-phenylbicyclo[2.2.2]oct-5-en-2-one (Compound 1)

| No. | Scale | Conditions | initial e.r.[1] | isolated e.r.[2] | yield |
|---|---|---|---|---|---|
| 5A | 36.2 g | TBME (0.8 vol.), 50° C., filtration at 0° C. | 69:31 | 98:2 | 33% |
| 5B | 3 g | TBME (1.7 vol.), 55° C., cool to 0° C., heptane (1.7 vol.), filtration at 0° C. | 98.3:1.7 | 99.7:0.3 | 50% |
| 5C | 3 g | TBME (1.0 vol.), 55° C., cool to 0° C., TBME (0.3 vol.), filtration at 0° C. | 98.3:1.7 | 99.6:0.4 | 87% |
| 5D | 2.2 g | TBME (1.4 vol.), 55° C., seeded with crystals of compound 1, filtration at 0° C. | 63:37 | 98:2 | 14% |

The filter cakes were washed with 2-3 × 0.1 vol. of the solvent used for the crystzallization.
[1] Ratio of 1:ent-1 of starting material
[2] Ratio of 1:ent-1 of isolated product.

Example 6

Preparation of rac-(1R*,4R*)-5-phenylbicyclo[2.2.2] oct-5-en-2-one (Compound rac-1)

6.1 Preparation of rac-(1R*,2S*,3S*,4R*)-6-oxo-3-phenylbicyclo[2.2.2]octan-2-yl methanesulfonate (Compound rac-5)

Compound rac-2 (171 g) was dissolved in DCM (1200 mL) followed by triethylamine (221 mL). The suspension was cooled to 0° C. and methane sulfonyl chloride (11.6 mL) was added at 10-20° C. After 1 h, the mixture was concentrated to dryness. The residue was taken up in iPrOAc (1 L) and water (1 L). The layers were separated and the aqueous phase was extracted with iPrOAc (500 mL). The combined org. extracts were concentrated under reduced pressure to yield compound rac-5 as a brown oil which was used in the next step without further purification. Yield: 208 g (crude yield), 89%. LC-MS method 2: 70% a/a, $t_R$=1.1. $^1$H-NMR (CDCl$_3$): corresponds to compound rac-5.

6.2 Preparation of rac-(1R*,4R*)-5-phenylbicyclo[2.2.2]oct-5-en-2-one (Compound rac-1)

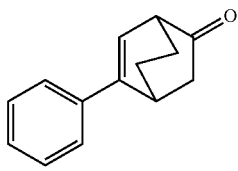 [SMILES: O=C1CC2CCC1C=C2c1ccccc1]

A soln. of compound rac-5 (190 g) in DMF (380 mL) was added at r.t. to a suspension of LiBr (56 g) and Li$_2$CO$_3$ (48 g) in DMF (570 mL). The resulting mixture was heated to 150° C. for 1 h. It was cooled down to r.t. Water (1300 mL) and iPrOAc (1300 mL) were added and the layers were separated. The organic layer was washed with brine (1300 mL), water (1300 mL) and concentrated to dryness under vacuum at 50° C. to yield compound rac-1. Yield: 117 g (crude yield), 91%. 108 g of this crude product was purified by short path distillation at 120° C. and 0.001 mbar to yield 47 g (37%) of compound rac-1. LC-MS method 2: 97% a/a, $t_R$=1.26. $^1$H-NMR (CD$_3$OD): δ=corresponds to compound rac-1.

The invention claimed is:

1. A process for the synthesis of (1R*,4R*,5S*,6S*)-6-hydroxy-5-arylbicyclo[2.2.2]octan-2-one compounds, the compounds of the formula (II):

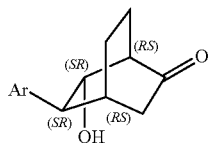

Formula (II)

said process comprising a cyclization of:
2-cyclohexen-1-one, and
a compound of the formula Ar—CH$_2$—CHO, wherein Ar represents an aryl group;
wherein said process is conducted:
in absence of a chiral base;
in the presence of
proline; and
a solvent selected from the group consisting of an aromatic solvent, an ether solvent, a chlorinated organic solvent, and an ester; or a mixture thereof; wherein said solvent is present in an amount of about 1 to 10 vol with respect to 2-cyclohexen-1-one;
and either in the presence of an achiral base or in absence of a base;
wherein said compound of formula (II) is isolated from the reaction mixture by solid-liquid separation.

2. The process according to claim 1, wherein said process is conducted in the presence of an achiral base.

3. The process according to claim 2, wherein said achiral base is an achiral N-containing base.

4. The process according to claim 3, wherein said achiral N-containing base is selected from the group consisting of NR$^1$R$^2$R$^3$, wherein R$^1$, R$^2$, and R$^3$ independently represent achiral C$_1$-C$_8$-alkyl; 1,4-diazabicyclo[2.2.2]octane; 1,8-diazabicyclo[5.4.0]undec-7-en, 1,5-diazabicyclo(4.3.0)non-5-ene; and pyridine, wherein the pyridine is unsubstituted, or mono-, di-, or tri-substituted with methyl.

5. The process according to claim 1, wherein said process is performed in the presence of enantiomerically enriched D- or L-proline.

6. The process according to claim 5, wherein said process is performed in the presence of an aromatic solvent, or an ether solvent.

7. The process according to claim 2, wherein said achiral N-containing base is present in an amount of about 0.1 equ. to 0.5 equ. with respect to 2-cyclohexen-1-one.

8. The process according to claim 7, wherein proline is present in an amount of about 0.05 equ. to 0.5 equ. with respect to 2-cyclohexen-1-one.

9. The process according to claim 8, wherein said compound of the formula Ar—CH$_2$—CHO is present in an amount of about 1 equ. to 2 equ. with respect to 2-cyclohexen-1-one.

10. The process according to claim 9, wherein said solvent is present in an amount of about 5 to 7 vol with respect to 2-cyclohexen-1-one.

11. The process according to claim 10, wherein the pH of the reaction mixture is about 8 to 10.

12. The process according to claim 11, wherein said isolation from the reaction mixture by solid-liquid separation is achieved
by filtration of the precipitated product at the reaction temperature; or
by
1. cooling of the reaction mixture to a temperature below the reaction temperature and
2. filtration of the precipitated product.

13. The process according to claim 1, wherein the compound of the formula (II) is further transformed to a compound the formula (I):

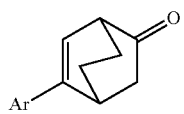

Formula (I)

wherein said transformation of the compound of the formula (II) to the compound of the formula (I) is effected via an elimination step.

14. The process according to claim 13, wherein the compound of formula (V):

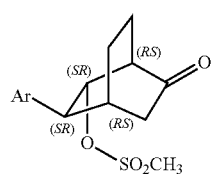

Formula (V)

is an intermediate of said elimination step.

15. The process according to claim 4, wherein said process is performed in the presence of enantiomerically enriched D- or L-proline.

16. The process according to claim 15, wherein the compound of the formula (II) is further transformed to a compound the formula (I):

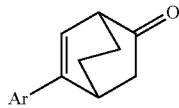

Formula (I)

wherein said transformation of the compound of the formula (II) to the compound of the formula (I) is effected via an elimination step.

17. The process according to claim 12, wherein the compound of the formula (II) is further transformed to a compound the formula (I):

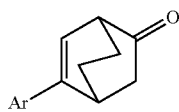

Formula (I)

wherein said transformation of the compound of the formula (II) to the compound of the formula (I) is effected via an elimination step.

18. The process according to claim 16, wherein the compound of formula (V):

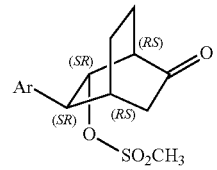

Formula (V)

is an intermediate of said elimination step.

19. The process according to claim 13, wherein the compound of the formula (I) wherein in this particular case Ar represents phenyl, is further transformed to any one of the following compounds:
rac-isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester,
isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester; or
isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester.

20. The process according to claim 15, wherein said achiral N-containing base is present in an amount of about 0.1 equ. to 0.5 equ. with respect to 2-cyclohexen-1-one.

* * * * *